US011219593B2

(12) United States Patent
Herrmann et al.

(10) Patent No.: US 11,219,593 B2
(45) Date of Patent: Jan. 11, 2022

(54) YARROW FRESH-PLANT PRESSED JUICE CONCENTRATE, PRODUCTION, AND USE

(71) Applicant: SYMRISE AG, Holzminden (DE)

(72) Inventors: Martina Herrmann, Hameln (DE); Sandra Gaebler, Höxter (DE); Manuel Pesaro, Beverungen (DE); Dominik Stuhlmann, Holzminden (DE); Lisa Garbe, Holzminden (DE); Julia Meyer, Dörentrup (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/608,907

(22) PCT Filed: Apr. 28, 2017

(86) PCT No.: PCT/EP2017/060175
§ 371 (c)(1),
(2) Date: Oct. 28, 2019

(87) PCT Pub. No.: WO2018/196993
PCT Pub. Date: Nov. 1, 2018

(65) Prior Publication Data
US 2020/0188290 A1 Jun. 18, 2020

(51) Int. Cl.
| | | |
|---|---|---|
| *A61K 36/28* | (2006.01) |
| *A61K 8/9789* | (2017.01) |
| *A23L 2/04* | (2006.01) |
| *A23L 2/08* | (2006.01) |
| *A23L 2/10* | (2006.01) |
| *A23L 2/12* | (2006.01) |
| *A61K 9/00* | (2006.01) |
| *A61K 47/36* | (2006.01) |
| *A61Q 5/00* | (2006.01) |
| *A61Q 19/00* | (2006.01) |

(52) U.S. Cl.
CPC .............. *A61K 8/9789* (2017.08); *A23L 2/04* (2013.01); *A23L 2/085* (2013.01); *A23L 2/102* (2013.01); *A23L 2/12* (2013.01); *A61K 9/0014* (2013.01); *A61K 36/28* (2013.01); *A61K 47/36* (2013.01); *A61Q 5/00* (2013.01); *A61Q 19/00* (2013.01)

(58) Field of Classification Search
CPC .... A61K 8/9789; A61K 9/0014; A61K 36/28; A61K 47/00; A61Q 5/00; A61Q 19/00; A23L 2/04; A23L 2/085; A23L 2/102; A23L 2/12
See application file for complete search history.

(56) References Cited

U.S. PATENT DOCUMENTS

| | | | | |
|---|---|---|---|---|
| 2013/0251884 A1* | 9/2013 | Langrish | ................. | A23L 19/01 426/616 |
| 2015/0313835 A1* | 11/2015 | Rana | ...................... | A61K 36/23 424/62 |

FOREIGN PATENT DOCUMENTS

| | | | | |
|---|---|---|---|---|
| DE | 1926166 A1 * | 11/1970 | ............. | A61K 36/28 |
| JP | H-11-199500 A | 7/1999 | | |
| JP | H-11-246347 A | 9/1999 | | |
| JP | 2000-505786 A | 5/2000 | | |
| JP | 2001-114637 A | 4/2001 | | |
| JP | 2004250354 A | 9/2004 | | |
| KR | 2015061818 A * | 6/2015 | | |
| WO | 9733596 A1 | 9/1997 | | |
| WO | 9742963 A2 | 11/1997 | | |

OTHER PUBLICATIONS

Haughton, *Achillea millefolium* (L), Nov. 27, 2014, www.purplesage.org.uk, pp. 1-5 (Year: 2014).*
International Search Report and Written Opinion dated Aug. 9, 2017 for corresponding PCT Application No. PCT/EP2017/060175.
Tessarollo et al., "Fitodefensivos em plantas medicinais", 2013, pp. 180-187 XP055378403.
Japanese Office Action dated Apr. 3, 2021 for corresponding Japanese Application No. 2019-558768.

* cited by examiner

*Primary Examiner* — Ali Soroush
(74) *Attorney, Agent, or Firm* — Polsinelli PC

(57) ABSTRACT

The present invention relates to a yarrow fresh plant press juice concentrate and a gentle method for its manufacture. The yarrow fresh plant press juice concentrate is used in cosmetic compositions, pharmaceutical compositions, food compositions or food supplements. This invention also relates to new aspects of the use of yarrow. The invention provides the use of yarrow to stimulate the expression of heat shock proteins and/or antimicrobial peptides in skin cells. It also describes the use of yarrow to increase the thermal tolerance of the skin.

14 Claims, No Drawings

YARROW FRESH-PLANT PRESSED JUICE CONCENTRATE, PRODUCTION, AND USE

CROSS-REFERENCE TO RELATED APPLICATIONS

This application is a national stage application (under 35 U.S.C. § 371) of PCT/EP2017/060175, filed Apr. 28, 2017, which is incorporated herein by reference in its entirety.

The present invention relates to a yarrow fresh plant press juice concentrate, which can be stored long-term without having to resort to thermal treatment, preservatives or other additives. Furthermore, the invention relates to a gentle method for manufacturing such yarrow fresh plant press juice concentrate. The yarrow fresh plant press juice concentrate is used in cosmetic compositions, pharmaceutical compositions, food compositions or food supplements.

The present invention also relates to new aspects of the use of yarrow. The invention provides the use of yarrow to stimulate the expression of heat shock proteins and/or antimicrobial peptides in skin cells. Furthermore, the use of yarrow to increase the thermal tolerance of the skin is described.

Yarrow (*Achillea millefollium*) is a traditional medicinal plant. Typical ingredients comprise, for example, essential oils, sesquiterpenes, phenolic compounds such as for example flavonoids, phenolcarboxylic acids, and betaines. Examples of phenolcarboxylic acids comprise chlorogenic acid and various dicaffeoylquinic acids.

Yarrow is used in the form of extracts. For the production of liquid extracts, for example, fresh (not dried) plants are used, i.e. in general the starting plant material must be cultivated or collected close to the production area. The ripe plants are harvested and must be pressed and bottled in a timely manner (usually within one day) to prevent spoilage and microbial contamination.

Yarrow press juice obtained in this way can be used, for example, for mild spasmodic discomfort in the gastrointestinal tract, including flatulence and loss of appetite. Yarrow is also used in skin creams for its positive properties in wound healing.

Yarrow extracts are already widely used in cosmetics for topical applications. These are extracts produced from the dried drug. Drying offers time independence from the seasonal harvest period and protection against possible spoilage. Dry plant material can be stored and transported more easily and cost-effectively. However, both during the drying of the plant material and during the production of the extract (extraction, if necessary with heat supply and usually subsequent distillative removal of the extraction agent under heating for concentration), partial changes in the spectrum of constituents of the plant take place.

The industrial production of yarrow fresh plant press juices is generally carried out by harvesting the plants or parts of plants to be pressed, cleaning, shredding, steam treatment to inactivate plant enzymes and decomposition of the plant material, pressing under pressure, filtration or centrifugation, ultra high-short-term heating for sterilisation and aseptic filling (Deutsche Apothekerzeitung 2011, p. 93 ff.). Such fresh plant press juices usually contain 2-6 wt.-% dry extract or dry juice. It is a gentle process in which higher temperatures are only used for a short time. Furthermore, comparatively few working steps are required. This is to ensure protection of sensitive, biologically active ingredients such as antioxidants.

A disadvantage is that the fresh plant press juice obtained can only be stored well in a closed container, otherwise there is a risk of microbial contamination. As a result, fresh plant press juice is problematic to handle, especially for the end consumer. This is due to the fact that either the complete consumption is necessary or the addition of undesirable preservatives to the fresh plant press juice is necessary to protect against spoilage.

Therefore, one object of the present invention is to provide long-term storable yarrow extracts and a method for manufacturing such extracts. A further object is to provide a yarrow extract that can be stored without the use of preservatives or other additives. The profile of the ingredients should not be affected by the manufacturing process or storage. Furthermore, an aqueous yarrow extract should to be provided, which offers additional, advantageous applications in comparison to the application possibilities known in the state of the art. The state of the art describes active substances for the stimulation of heat shock proteins and/or cutaneous AMPs. Nevertheless, there is a need for new natural, well-tolerated HSP and/or AMP stimulators that are easy to introduce into cosmetic formulations.

The invention therefore relates to a yarrow fresh plant press juice concentrate comprising or consisting of:
10-100 wt.-% yarrow fresh plant press juice dry residue,
0-90 wt.-% water, and
0-90 wt.-% carrier(s),
based on 100 wt.-% of the yarrow fresh plant press juice concentrate.

Further, the invention relates to a method for manufacturing a yarrow fresh plant press juice concentrate, preferably a concentrate according to the invention as described herein, comprising the steps or consisting of the steps:
Providing a yarrow of fresh plant press juice, and
Concentrating the yarrow fresh plant press juice.

The invention provides the use of yarrow for stimulating the expression of heat shock proteins and/or antimicrobial peptides in skin cells.

The invention further provides for the use of yarrow for increasing the thermal tolerance of the skin.

Furthermore, the present invention relates the use of the fresh plant press juice concentrate according to the invention as a medicament.

Surprisingly, it was found that concentrates of yarrow fresh plant press juice dry residue have a long shelf life. This is even the case when omitting preservatives or respective treatment procedures at elevated temperatures, e.g. pasteurization, for preserving. The method according to the invention allows the gentle (i.e. no prolonged exposure at higher temperatures) method of preserving the ingredient profile. In particular, reverse osmosis, freeze drying, spray drying or a combination of these concentration processes can be used.

The use of one or more of these methods can prevent the use of unfavourable practices for the concentration of fresh plant press juice, such as the removal of water by distillation. The distillative removal of water requires a longer process time at elevated temperatures (70-80° C.), which usually leads to changes in the ingredient profile. Thermally sensitive ingredients can thereby change or be degraded.

It has also been found that yarrow in general, and in particular the concentrates and yarrow fresh plant press juices according to the invention, are suitable for cosmetic compositions. Yarrow, in particular yarrow fresh plant press juice, upregulates some heatshock proteins (HSPs) at gene level. Thus, HSP70 is not upregulated, but HSP27 is upregulated at the gene level. Furthermore, it was surprisingly found that yarrow, especially yarrow fresh plant press juice, upregulates antimicrobial proteins and peptides (AMPs), such as for example beta-defensin 1 and S100 calcium binding protein A8, at gene level. It is known that Hsp27 provides thermal tolerance and cytoprotection and supports cell survival under stress conditions. AMPs, on the other hand, can be used as topically applied biocides, in particular for the treatment of multi-resistant pathogens and for the treatment of skin and wound infections. Furthermore, its use in tumor therapy is conceivable. This leads to advantageous applications of yarrow, especially in the framework of cosmetic compositions and pharmaceutical compositions, which are preferably applied topically.

The term "yarrow" as used herein refers to *Achillea millefollium* herb or yarrow herb and also the members of the *Achillea millefollium* group according to Hager's Handbuch der pharmazeutischen Praxis, Springer Verlag. Yarrow can be present as untreated plant or in various preparations, e.g. yarrow fresh plant press juice or yarrow fresh plant press juice concentrate.

The "yarrow fresh plant press juice" and the "yarrow fresh plant press juice concentrate" are characterised by the presence of a relatively high content of polyphenols, especially phenolcarboxylic acids including the group of monocaffeoylquinic acids (containing chlorogenic acid [3-O-caffeoylquinic acid, CAS 327-97-9], neochlorogenic acid [5-O-caffeoylquinic acid, CAS 906-33-2] and cryptochlorogenic acid [4-O-caffeoylquinic acid, CAS 905-99-7]) and the group of dicaffeoylquinic acids (containing 1,5-di-O-caffeoylquinic acid [cynarin, CAS 30964-13-7], 3,4-di-O-caffeoylquinic acid [isochlorogenic acid B, CAS 14534-61-3], 3,5-di-O-caffeoylquinic acid [isochlorogenic acid A, CAS 2450-53-5] and 4,5-di-O-dicaffeoylquinic acid [isochlorogenic acid C, CAS 57378-72-0]). Polyphenols are known for their very good anti-oxidative efficacy.

Yarrow fresh plant press juice can, for example, be obtained from the company Schoenenberger (user information: Natural unadulterated medicinal plant juice yarrow for use by adults and adolescents over 12 years of age, Walther Schoenenberger Pflanzensaftwerk GmbH & Co. KG, Magstadt (Germany), July 2014). The yarrow fresh plant press juice is produced from fresh yarrow herb harvested during the flowering period. It is marketed for oral use as a traditional herbal medicinal product for mild spasmodic discomforts in the gastrointestinal tract including flatulence and loss of appetite. The yarrow fresh plant press juice is a brown, clear to slightly opalescent liquid and usually contains between 94.5-96.5 wt.-% water and 3.5-5.5 wt.-% dry residue.

Yarrow fresh plant press juice concentrate can, for example, be produced from yarrow fresh plant press juice by a concentration process. For example, yarrow fresh plant press juice concentrate is produced from yarrow fresh plant press juice of the company Schoenenberger by concentrating. However, it is clear that any yarrow extract, in particular yarrow fresh plant press juice, can be used.

The term "dry residue" or "dry substance" is used according to the definition in analytical chemistry for the water and/or solvent-free fraction of a substance remaining after drying, e.g. of a yarrow fresh plant press juice or yarrow fresh plant press juice concentrate. The drying process is essentially complete, i.e. a remaining water and/or solvent content of the analyzed substance, for example of a yarrow fresh plant press juice or yarrow fresh plant press juice concentrate, is preferably ≤1 wt.-%, preferably ≤0.5 wt.-%, ≤0.1 wt.-%, more preferably ≤0.01 wt.-%. Drying is preferably carried out by gentle processes, e.g. by a slightly increased temperature, such as ≤10° C., ≤5° C. or ≤2° C., than the boiling point of water, the solvent or, if applicable, the solvent mixture. Alternative drying methods include freeze drying, drying under partial vacuum, the use of desiccants or a combination of the above methods.

The term "extract" as used herein relates to thickened or dried extracts of plant substances, in particular of yarrow. Therefore, an extract is a liquid. Yarrow fresh plant press juice represents such an extract. Yarrow fresh plant press juice preferably contains ≤8 wt.-% dry residue, preferably ≤7.5 wt.-% dry residue, ≤7 wt.-% dry residue, ≤6.5 wt.-% dry residue, ≤6 wt.-% dry residue or ≤5.5 wt.-% dry residue. More preferably, yarrow fresh plant press juice contains ≤3.5 wt.-% to ≤5.5 wt.-% dry residue.

The term "concentrate" as used herein relates to a solid or a liquid with a relatively low proportion of additional fillers and/or solvents. Yarrow fresh plant press juice concentrate is therefore characterised by a higher dry residue than yarrow fresh plant press juice. Yarrow fresh plant press juice concentrate has ≥10 wt.-% dry residue, preferably ≥15 wt.-% dry residue, ≥20 wt.-% dry residue, ≥25 wt.-% dry residue, ≥30 wt.-% dry residue, ≥40 wt.-% dry residue, ≥50 wt.-% dry residue, ≥60 wt.-% dry residue, ≥70 wt.-% dry residue, ≥80 wt.-% dry residue, or 90 wt.-% dry residue. The concentrate is produced gently, i.e. in comparison to the extract essentially the same content spectrum of components remains accordingly concentrated (according to the ratio of dry residue concentrate divided by dry residue extract). Essentially the same content spectrum of components relates to individual deviations of the components of ±10 wt.-% in the concentrate, preferably ±5 wt.-% in the concentrate, more preferably ±2 wt.-% in the concentrate. If, for example, yarrow fresh plant press juice has a dry residue of 8 wt.-% and yarrow fresh plant press juice concentrate has a dry residue of ≥10 wt.-%, the concentration of the individual components or ingredients in the concentrate is at least increased by a factor of 10 divided by 8.

Solid yarrow fresh plant press juice concentrate comprises, based on 100 wt.-% yarrow fresh plant press juice concentrate, 10-100 wt.-% yarrow fresh plant press juice dry residue, 0-90 wt.-% water, and 0-90 wt.-% carrier based on 100 wt.-% of the yarrow fresh plant press juice concentrate. Preferably, solid yarrow fresh plant press juice concentrate is produced directly, i.e. without prior concentration, with the optional addition of the carriers mentioned herein. Such solid yarrow fresh plant press juice concentrate comprises 10-100 wt.-% yarrow fresh plant press juice dry residue, 0-10 wt.-% water, and 0-90 wt.-% carrier. More preferably the solid yarrow fresh plant press juice concentrate comprises 10-50 wt.-% yarrow fresh plant press juice dry residue, 0-10 wt.-% water, and 50-90 wt.-% carrier.

Liquid yarrow fresh plant press juice concentrate is preferably produced by reverse osmosis and subsequent addition of a liquid carrier and preferably comprises 10-70 wt.-% yarrow fresh plant press juice dry residue, 0-90 wt.-% water, 0-90 wt.-% liquid carrier, and 0-5 wt.-% preservatives and/or stabilizers. The optional liquid carrier(s) is/are as set forth hereinbelow and is/are or comprise(s) e.g. glycerol, propylene glycol, butylene glycol, 1,3-propanediol, 1,2-pentanediol, 1,2-hexanediol and is/are added as well as the optional preservative and/or stabilizer after concentration.

Preferred is liquid yarrow fresh plant press juice concentrate comprising 10-50 wt.-% yarrow fresh plant press juice dry residue, 0-90 wt.-% water, 0-50 wt.-% carrier, 0-3 wt.-% preservative and/or stabilizers. The advantage of solid or liquid yarrow fresh plant press juice concentrate is its simple and cost-effective production, good storability, easy handling and dosing and, if desired, standardization.

The dosage of (liquid or solid) yarrow fresh plant press juice concentrate in cosmetic compositions, in particular in cosmetic compositions for cleansing and caring for skin and hair, is 0.0001-10 wt.-%, preferably 0.001-5 wt.-% and particularly preferably 0.005-3 wt.-%.

Cosmetic compositions preferably have 0.0001-10 wt.-%, preferably 0.001-5 wt.-% and particularly preferably 0.005-3 wt.-% yarrow fresh plant press juice concentrate, whereby the concentrate can be obtained by freeze drying, spray drying or reverse osmosis. These cosmetic compositions also contain one of the ingredient combinations mentioned in Example 5, Table 12, Compositions 1-11, whereby the individual amount of the respective ingredients besides the yarrow fresh plant press juice concentrate can be freely selected. It is clear that the perfume combinations used are not limited to the perfume oils PFO1 and PFO2, but also other perfumes or perfume combinations known to the skilled person can be used.

Alternatively, a gel toothpaste can be present. It also contains 0.0001-10 wt.-%, preferably 0.001-5 wt.-% and particularly preferably 0.005-3 wt.-% yarrow fresh plant press juice concentrate, whereby the concentrate can be obtained by freeze drying, spray drying or reverse osmosis. This composition also contains one of the ingredient combinations mentioned in example 5, table 13, compositions I, II and III, whereby the individual amount of the respective ingredients besides the yarrow fresh plant press juice concentrate can be freely selected.

Alternatively, a ready-to-use mouthwash with fluoride can be present. It also contains 0.0001-10 wt.-%, preferably 0.001-5 wt.-% and particularly preferably 0.005-3 wt.-% yarrow fresh plant press juice concentrate, whereby the concentrate can be obtained by freeze drying, spray drying or reverse osmosis. This composition also contains one of the ingredient combinations mentioned in example 5, table 14, compositions I, II and III, whereby the individual amount of the respective ingredients besides the yarrow fresh plant press juice concentrate can be freely selected.

Alternatively, the yarrow fresh plant press juice concentrate according to the invention consists of the mentioned ingredients. In this case no other ingredients are present. Thus, the yarrow fresh plant press juice concentrate according to invention consists of, based on 100 wt.-% yarrow fresh plant press juice concentrate, 10-100 wt.-% yarrow fresh plant press juice dry residue, 0-90 wt.-% water, and 0-90 wt.-% carrier. Preferably, the yarrow fresh plant press juice concentrate according to the invention consists of 10-50 wt.-% yarrow fresh plant press juice dry residue, 0-50 wt.-% water, and 0-50 wt.-% carrier; 10-20 wt.-% yarrow fresh plant press juice dry residue, 0-80 wt.-% water, and 0-80 wt.-% carrier; 10-15 wt.-% yarrow fresh plant press juice dry residue, 0-85 wt.-% water, and 0-85 wt.-% carrier. More preferably, the yarrow fresh plant press juice concentrate according to the invention consists of 10-15 wt.-% yarrow fresh plant press juice dry residue, as well as 85-95 wt.-% water and/or carrier.

According to one embodiment, the carrier(s) is/are a solid carrier, in particular maltodextrin, dextrin or cyclodextrin, and/or a liquid carrier, in particular glycerol, propylene glycol, butylene glycol, 1,3-propanediol, 1,2-pentanediol, 1,2-hexanediol or 1,2-octanediol.

The addition of carriers or carrier material allows the product properties (e.g. flowability) and/or standardization to be influenced to a certain extent. Besides, the resulting matrix particles also provide a certain protection for labile ingredients. The carrier is preferably chosen such that it is used in the course of the concentration. If, for example, concentration is done by spray drying, a solid carrier, in particular one of the polysaccharides listed below, may be used as a suitable material. This polysaccharide can in turn serve as a carrier in a cosmetic composition, for example, which gives the composition the desired properties. More preferably, a carrier substance is used in the context of the concentration which is used in the desired dosage form, e.g. in a cosmetic composition, pharmaceutical composition, food composition or in a food supplement.

It is clear that one or several carriers can be contained. These carriers can be solid or liquid (at 25° C. and 1013 mbar). Individual substances or mixtures of substances can be used as carriers.

Advantageous solid carriers are degraded starches, chemically or physically modified starches, modified celluloses, gum arabic, ghatti gum, traganth, karaya, carrageenan, guar gum, locust bean gum, alginates, pectin, inulin or xanthan gum. In general, polysaccharides such as for example maltodextrin, dextrin, oxidized starch or lactose, collagen, fumed silica (such as an Aerosil®), cashew gum, gum arabic or similar can be used. Mixtures of the above-mentioned solid carriers may also be used in the context of this invention. Maltodextrin is a particularly preferred solid carrier.

The degree of decomposition of starch is usually indicated by the index 'dextrose equivalent' (DE), which has the threshold values 0 for a long-chain glucose polymer and 100 for pure glucose. Polysaccharides, in particular maltodextrin, with DE values in the range of 5 to 20, preferably in the range of 15 to 20, are again particularly advantageous.

Examples of preferred liquid carriers are ethanol, diacetin, isopropyl alcohol, glycerol, 1,2-propylene glycol, 1,3-propanediol, 1,3-butylene glycol, triacetin and mixtures thereof.

Advantageous carriers in the preferred (preferably spray-dried) concentrates according to the invention are in particular silicon dioxide (silicic acid, silica gel), carbohydrates and/or carbohydrate polymers (polysaccharides), cyclodextrins, starches, degraded starches (starch hydrolysates), chemically or physically modified starches, modified celluloses, gum arabic, ghatti gum, traganth, karaya, carrageenan, guar gum, locust bean gum, alginates, pectin, inulin or xanthan gum. Preferred starch hydrolysates are maltodextrins and dextrins. Particularly preferred carriers are silicon dioxide, gum arabic and maltodextrins, whereby maltodextrins with DE values in the range of 5 to 20 are preferred.

The preferred or particularly preferred carriers also have the advantage that they are tasteless or essentially tasteless. As a result, concentrates according to the invention can be used in many different product types and preparations, since these precursors do not or not significantly influence the other sensory profiles, in particular the aroma and taste profile—apart from the unpleasant taste impressions to be masked.

According to one embodiment, the yarrow fresh press plant juice concentrate further comprises preservatives and/or stabilizers.

Any number of preservatives and/or stabilizers can be used.

Preservatives used in the context of this invention usually have several, preferably all, of the following properties. They are toxicologically harmless, well tolerated by the skin, stable, essentially completely odourless and can be produced easily and inexpensively (i.e. from easily accessible educts). The preservative may also have antimicrobial properties. Suitable preservatives can be found for example in WO 2006/045743.

Examples of suitable preservatives include benzoic acid, the esters and salts of benzoic acid, sorbic acid and its salts, propionic acid and its salts, salicylic acid and its salts, dormaldehyde and paraformaldehyde, 2-hydroxybiphenyl ether and its salts, 2-zinc sulfidopyridine N-oxide, inorganic sulfites and bisulfites, sodium iodate, chlorobutanol, 4-ethylmercury(II)-5-amino-1,3-bis(2-hydroxybenzoic acid), the esters and salts thereof, dehydroxyacetic acid, formic acid, 1,6-bis(4-amidino-2-bromophenoxy)-n-hexane and its salts, the sodium salt of ethylmercury(II)-thiosalicylic acid, phenylmercury and its salts, 10-undecylenic acid and its salts, 5-amino-1,3-bis(2-ethylhexyl)-5-methyl hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioximidazolidin-5-yl)urea), poly(hexamethylenebiguanide)hydrochloride, 2-phenoxyethanol, hexamethylenetetramine, 1 (3-chloroallyl)-3,5,7-triaza-1-azoniaadamantane chloride, 1(4-chlorophenoxy) 1(1H-imidazole-1-yl)-3,3-dimethyl-2-butanone, 1,3-bis(hydroxymethyl)-5,5-dimethyl-2,4-imidazolidin-edione, benzyl alcohol, octopirox, 1,2-dibromo-2,4-dicyanobutane, 2,2'-methylene-bis(6-bromo-4-chlorophenol), bromochlorophene, mixture of 5-chloro-2-methyl-3(2H)isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl(C12-C22)trimethylammoniumbromide and chloride, 4,4-dimethyl-1,3-oxazolidine, N-hydroxymethyl-N-(1,3-di (hydroxymethyl)-2,5-dioxoimidazolidin-4-yl)-N'-hydroxymethyl urea, 1,6-bis(4-amidino-phenoxy)-n-hexane and its salts, glutaraldehyde, 5-ethyl-1-aza-3,7-dioxa-bicyclo(3.3.0)octane, 3-(4-chlorophenoxy)-1,2-propanediol, hyamine, alkyl-(C8-C18)-dimethylbenzylammonium chloride, alkyl-(C8-C18)-dimethylbenzylammonium bromide, alkyl-(C8-C18)-dimethylbenzylammonium saccharinate, benzylhemiformal, o-cymen-5-ol, sodium hydroxymethylaminoacetate or sodium hydroxymethylaminoacetate, and mixtures of the above mentioned substances.

Other suitable preservatives include parabens. Parabens are esters of para-hydroxybenzoic acid, such as methyl paraben, ethyl paraben, n-propyl paraben, n-butyl paraben, isobutyl paraben and mixtures. Parabens may be used alone or in combination as preservatives, particularly in cosmetic and pharmaceutical compositions. A preferred combination of parabens with regard to the above mentioned compositions comprises 18 wt.-% methyl parabens and 0.02 wt.-% propyl parabens. Parabens have both an antimicrobial and a fungicidal effect.

In addition, preservatives or preservative excipients commonly used in cosmetics are suitable according to the invention, such as dibromodicyanobutane (2-bromo-2-bromomethylgl utarodinitrile), 3-iodo-2-propinyl butylcarbamate, 2-bromo-2-nitro-propane-1,3-diol, imidazolidinylurea, 5-chloro-2-methyl-4-isothiazolin-3-one, 2-chloroacetamide, benzalkoniumchloride, benzyl alcohol and formaldehyde splitters.

In addition, phenylhydroxyalkyl ethers, in particular the compound known as phenoxyethanol, are suitable as preservatives because of their bactericidal and fungicidal effects on a number of micro-organisms.

Stabilizers are used in the context of the present invention to protect the compositions according to the invention against external environmental influences. Such environmental influences include, for example, atmospheric oxygen and light irradiation, especially sunlight. The oxidative effect of atmospheric oxygen can, for example, be counteracted with suitable antioxidants. Photostabilizers can be used to counter the harmful effects of light irradiation.

The protective effect of some benzoic acids and their salts has been known for a long time. They are, amongst others, used in foods mainly for microbiological stabilization in acidic applications and are known as E 210 (benzoic acid), E211 (sodium benzoate), E212 (potassium benzoate) and E213 (calcium benzoate). Also various parabens (hydroyxbenzoic acid esters) under the numbers E 214 (ethyl-p-hydroxybenzoate), E215 (sodium ethyl-p-hydroxy benzoate), E218 (methyl-p-hydroxybenzoate) and E219 (sodium methyl-p-hydroxy benzoate) are used in foods to improve microbiological stability (BGBl. I 2000, 1537-1545). This substance class is also widely used in cosmetics for the purpose of improving (microbiological) stability.

Suitable stabilisers can also be taken from, for example, in DE 299 24 656, DE 699 17 811, DE 696 24 799, EP 2 952 103 and DE 695 18 581.

In accordance with one embodiment, the yarrow fresh plant press juice is concentrated at a temperature of <60° C.

Concentrating can be performed under normal pressure (1013 mbar) or under partial negative pressure, e.g. 100 to 1000 mbar, preferably 200 to 500 mbar. Preferably, concentrating of the yarrow fresh plant press juice takes place at a temperature of <55° C., more preferably <50° C., <45° C., <40° C., <35° C., <30° C., <25° C., even more preferably <10° C., <0° C., or <20° C. The combination of a partial negative pressure with a low temperature is particularly preferred due to the gentle treatment of the concentrate.

According to one embodiment, the yarrow fresh plant press juice is concentrated by a concentration process selected from freeze drying, spray drying and reverse osmosis or a combination thereof. These processes are well known in the state of the art.

It has been shown that reverse osmosis is particularly advantageous due to the gentle concentration of the aqueous solutions for the manufacture of the water-based extract/juice concentrates according to the invention. Reverse osmosis, also known as hyperfiltration, is usually performed with membranes of PAN (polyacrylonitrile), PES (polyethersulfone) and/or PVDF (polyvinylidene difluoride) with a NaCl exclusion rate of ≥90%, preferably ≥95%, ≥97%, more preferably 99%, an operating flow of 8 l/m$^2$/h to 34l/m$^2$/h, preferably 8l/m$^2$/h to 25l/m$^2$/h, 8l/m$^2$/h to 20l/m$^2$/h pressure, more preferably 8 l/m$^2$/h to 15 l/m$^2$/h at a pressure of 15 to 50 bar, preferably 15 to 40 bar, more preferably 15 to 35 bar and a temperature of 60° C., preferably 50° C., 40° C., more preferably 30° C.

It is also advantageous to protect these concentrates from microbial contamination. This can be achieved, for example, by lowering the pH value and/or addition of suitable preservatives as described above.

Freeze drying, also called lyophilization or sublimation drying, is an extremely gentle process, albeit cost-intensive and relatively complex. Freeze drying is based on the physical process of sublimation: The ice crystals thereby sublime directly into the gaseous state without the occurrence of a liquid phase in between. In the present case, freeze drying produces a well storable solid even without the addition of preservatives. Procedures for freeze drying can be taken from, for example, GB 1 447 988 and DE 198 17 177.

In spray drying, for example in a fluidized bed, the material to be dried is introduced into a hot gas stream by means of a vaporizer, which dries it into a fine powder in a very short time (a few seconds to fractions of a second). Spray drying can optionally take place with the addition of the above-mentioned carriers such as maltodextrin, cyclodextrin, etc. The advantage here is that it is an established procedure that can be carried out cost-effectively. Only a very brief exposure, e.g. for a few seconds, preferably less than 3 seconds or less than 1 second, at higher temperatures, e.g. 200-400° C., preferably 250-270° C., is required. A solid that can be well stored without the addition of preservatives is obtained.

The yarrow fresh plant press juice concentrate is preferably obtainable through the method according to the invention.

According to one embodiment, a cosmetic composition, pharmaceutical composition, food composition or food supplement is provided. The pharmaceutical composition, food composition or food supplement comprise the yarrow fresh plant press juice concentrate according to the invention, respectively. The cosmetic composition comprises yarrow fresh plant press juice or the yarrow fresh plant press juice concentrate according to the invention.

The concentrates according to the invention have a wide range of applications in human cosmetics and care, especially skin and hair care, but can also be used pharmacologically as well as in foods and food supplements.

Cosmetic compositions may be, in particular, skin cosmetic, hair cosmetic, dermatological and hygienic compositions. In particular, the concentrates according to the invention are used for skin and/or hair cosmetics.

The hair or skin caring compositions or preparations according to the invention are preferably in the form of an emulsion, a dispersion, a suspension, in the form of an aqueous surfactant preparation, a milk, a lotion, a cream, a balm, an ointment, a gel, a granulate, a powder, a stick preparation such as e.g. a lipstick, a foam, an aerosol or a spray. Such formulations are well suited for topical preparations. Oil-in-water emulsions and water-in-oil emulsions or microemulsions can be used as emulsions.

In general, the hair or skin cosmetic preparation is used for application on the skin or hair. "Topical preparations" means preparations which are suitable for applying the active substances to the skin in a finely distributed form, such as e.g. in a form that is absorbable through the skin. Suitable are e.g. aqueous and aqueous-alcoholic solutions, sprays, foams, foam aerosols, ointments, aqueous gels, emulsions of the O/W or W/O type, microemulsions or cosmetic stick preparations.

The cosmetic composition may contain one (or several) carrier(s). Preferred as carrier is water, a gas, a water-based liquid, an oil, a gel, an emulsion or microemulsion, a dispersion or a mixture thereof. The carriers mentioned show a good skin compatibility. Especially advantageous for topical preparations are aqueous gels, emulsions or microemulsions. The carrier may also be in the form of a homogeneous phase formulation or in the form of an emulsion. The emulsion can be an oil-in-water, water-in-oil or multi-phase emulsion. These emulsions can be used in a wide range of consistencies including fluid lotions (which can also be administered as a spray or aerosol), creamy lotions, light and heavy creams and the like. Other suitable carriers comprise anhydrous liquid solvents such as e.g. oils and alcohols, water-based single phase liquid solvents (e.g. hydroalcoholic solvent systems), anhydrous solids and semisolids (e.g. gels and sticks) and water-based gel and foam systems. Examples of carriers and carrier systems suitable within the framework of the present invention can be taken from, for example, "Sun Products Formulary" Cosmetics & Toiletries, Vol. 105, p. 122-139 (December 1990); "Sun Products Formulary", Cosmetics & Toiletries, Vol. 102, p. 117-136 (March 1987); U.S. Pat. No. 4,960,764, Figueroa et al.; and U.S. Pat. No. 4,254,105, Fukuda et al.

The teaching according to the invention also comprises the use of the concentrates described herein in a pharmaceutical composition. This pharmaceutical composition may be used as a medicament for the treatment of an individual, preferably a mammal, in particular a human. The pharmaceutical composition usually comprises a pharmaceutically acceptable excipient with the concentrate according to the invention and, where appropriate, one or several other active substances.

These compositions can be administered orally and transdermally, for example. Examples of suitable pharmaceutical formulations are solid dosage forms such as powder, powders, granules, tablets, pastilles, sachets, cachets, dragees, capsules such as hard and soft gelatin capsules, semi-solid dosage forms such as ointments, creams, hydrogels, pastes or plasters, as well as liquid dosage forms such as solutions, emulsions, in particular oil-in-water emulsions, and suspensions such as lotions.

In the manufacture of compositions according to the invention, components or active substances to be used according to the invention are usually mixed or diluted with an excipient. Excipients may be solid, semi-solid or liquid materials which serve as vehicles, carriers or media for the active substances contained in the concentrate. The active substance content (of one or several simultaneously contained active substances according to the invention) can vary over a wide range.

Suitable excipients include lactose, dextrose, sucrose, sorbitol, mannitol, starches, acacia gum, calcium phosphate, alginates, traganth, gelatin, calcium silicate, microcrystalline cellulose, polyvinylpyrrolidone, cellulose, water, syrup and methylcellulose. In addition, the formulations may comprise pharmaceutically acceptable carriers or common excipients such as lubricants, for example tallow, magnesium stearate and mineral oil; wetting agents; emulsifiers and suspending agents; preservatives such as methyl and propyl hydroxybenzoates; antioxidants; anti irritants; chelating agents; coating aids; emulsion stabilizers; film-forming agents; gelling agents; odour masking agents; flavour correctives; resins; hydrocolloids; solvents; solubilizers; neutralizers; permeation accelerators; pigments; quaternary ammonium compounds; refatting and superfatting agents; ointment, cream or oil bases; silicone derivatives; spreading aids; stabilizers; sterilants; suppository bases; tablet auxiliaries, such as binders, fillers, lubricants, disintegrants or coatings; propellants; desiccants; opacifiers; thickeners; waxes; plasticizers; white oils. The design in this respect is based on the knowledge of the skilled person, as for example shown in Fiedler, H. P., Lexikon der Hilfsstoffe für Pharmazie, Kosmetik and angrenzende Gebiete, 4th edition, Aulendorf: ECV-Editio-Kantor-Verlag, 1996, or Hager's Handbuch der Pharmazeutischen Praxis, Springer Verlag, Heidelberg.

Within the framework of the present invention, it is generally possible and regularly advantageous to combine the fresh plant press juice or concentrate according to the invention or to be used according to the invention with (other) (active) substances, e.g. selected from the group consisting of abrasives, anti-acne agents and sebum reduction agents, anti-aging agents, antibacterial agents, anti-cellulite agents, anti-dandruff agents, anti-inflammatory agents, irritation-preventing agents, anti-irritants (anti-inflammatory, irritation-inhibiting and irritation-preventing agents), antimicrobial agents, antioxidants, astringents, antiseptic agents, antistatic agents, binders, buffers, carriers, chelating agents, cell stimulants, cleansing agents, caring agents, depilatory agents, surface-active substances, deodorants and antiperspirants, plasticizers, emulsifiers, enzymes, essential oils, insect repellents, fibers, film formers, fixers, foaming agents, foam stabilizers, antifoaming agents, foam boosters, fungicides, gelling agents and gel-forming agents, hair care products, hair shaping agents, hair straightening agents, moisture regulators (moisturizing, wetting and/or moistening substances), osmolytes, compatible solutes, bleaching agents, strengthening agents, stain removing agents, optical brightening agents, impregnating agents, soil repellents, friction-reducing agents, lubricants, moisturizing creams, ointments, turbidity agents, plasticizers, opacifiers, polishes, brighteners, polymers, powders, proteins and protein hydrolysates, refattening agents, abrasive agents, skin soothing agents, skin cleansing agents, skin caring agents, skin repair agents, preferably containing cholesterol and/or fatty acids and/or ceramides and/or pseudoceramides, skin whitening agents, skin protecting agents, skin softening agents, skin cooling agents, preferably the skin warming agents mentioned in WO 2005/123101, UV absorbing agents and UV filters, preferably those mentioned in WO 2005/123101, benzylidene-beta-dicarbonyl compounds, alpha-benzoyl cinnamic acid nitriles, AhR receptor antagonists, detergents, fabric softeners, suspending agents, skin tanning agents, thickening agents, vitamins, oils, waxes and fats, phospholipids, fatty acids (saturated fatty acids, mono- or polyunsaturated fatty acids, α-hydroxy acids, polyhydroxy fatty acids), plasticizers, dyes and color protecting agents as well as pigments, anticorrosives, aromas and flavors as well as fragrances, preferably those listed in S. Arctander, Perfume and Flavor Chemicals, self-published, Montclair, N.J., 1969 and Surburg, Panten, Common Fragrance and Flavor Materials, 5th Edition, Wiley-VCH, Weinheim 2006, surfactants, animal extracts, yeast extracts, extracts of algae or microalgae, electrolytes, liquefiers, organic solvents, hair growth modulating agents (hair growth promoting or hair growth inhibiting) and silicones and silicone derivatives, preferably one or several skin cooling agents and/or one or several UV absorbing agents or UV filters.

Accordingly, the compositions according to the invention may also contain (further) cosmetically and/or dermatologically and/or pharmacologically active agents in addition to the usual additives or excipients.

Suitable cosmetically and/or dermatologically active agents are, for example, coloring agents, skin and hair pigmenting agents, tinting agents, tanning agents, bleaching agents, keratin-hardening substances, antimicrobial agents, light-filtering agents, hyperemising substances, keratolytic and keratoplastic substances, anti-dandruff agents, antiphlogistics, keratinising substances, antioxidative or substances active as radical scavengers, skin moisturising or moistening substances, refatting agents, antierythimatous or anti-allergic active agents, branched fatty acids such as 18-methyle-icosanoic acid, and mixtures thereof.

Artificial skin tanning agents which are suitable for tanning the skin without natural or artificial irradiation with UV rays; these are e.g. dihydroxyacetone, alloxane and walnut shell extract. Suitable keratin-hardening substances are usually agents such as those used in antiperspirants, such as e.g. potassium aluminium sulphate, aluminium hydroxychloride, aluminium lactate, etc.

Antimicrobial agents used to destroy or inhibit the growth of microorganisms. They thus serve both as preservatives and as a deodorizing substance, which reduces the development or intensity of body odor. These include, for example, common preservatives known to the skilled person, such as p-hydroxybenzoic acid ester, imidazolidinyl-urea, formaldehyde, sorbic acid, benzoic acid, salicylic acid, etc. Such deodorizing substances are e.g. zinc ricinoleate, triclosan, undecylenic acid alkylolamides, citric acid triethyl esters, chlorhexidine, etc.

The skilled person is familiar with suitable excipients and additives for the production of hair-cosmetic or skin-cosmetic preparations and can be taken from cosmetic manuals, for example Schrader, Grundlagen and Rezepturen der Kosmetika, Hüthig Verlag, Heidelberg, 1989, ISBN 3-7785-1491-1. The excipients and additives are preferably cosmetically and/or pharmaceutically acceptable excipients. Pharmaceutically acceptable are the excipients known to be applicable in the field of pharmacy, food technology and related fields, in particular those listed in relevant pharmacopoeias (e.g. DAB, Ph. Eur., BP, NF) as well as other excipients whose properties do not contradict physiological application.

Suitable excipients can be: Lubricants, wetting agents, emulsifying and suspending agents, preservatives, antioxidants, anti-irritants, chelating agents, emulsion stabilizers, film formers, gelling agents, odour masking agents, hydrocolloids, solvents, solubilizers, neutralizers, permeation accelerators, pigments, quaternary ammonium compounds, refatting and superfatting agents, ointment, cream or oil bases, silicone derivatives, stabilizers, sterilants, propellants, drying agents, opacifiers, thickeners, waxes, plasticizers and white oil.

Further suitable additives are selected from perfume oils, hair polymers, hair and skin conditioners, graft polymers, water-soluble or dispersible silicone-containing polymers, light protecting agents, bleaching agents, care agents, dyeing agents, tinting agents, tanning agents, dyestuffs, consistency enhancers, humectants, refattening agents, collagen, protein hydrolysates, lipids, antioxidants, defoamers, antistatics, emollients, plasticizers, peroxide decomposers.

As examples of suitable excipients and additives, the antioxidants, peroxide decomposers, thickeners and the preservatives listed above are to be listed.

Peroxide decomposers are compounds which chemically decompose peroxides, especially lipid peroxides. Examples comprise pyridine-2-thiol-3-carboxylic acid, 2-methoxy-pyrimidinol carboxylic acids, 2-methoxy-pyridinecarboxylic acids, 2-dimethylamino-pyrimidinolcarboxylic acids, 2-dimethylamino-pyridinecarboxylic acids.

Examples of thickeners are cross-linked polyacrylic acids and their derivatives, polysaccharides and their derivatives, such as xanthan gum, agar-agar, alginates or tyloses, cellulose derivatives, e.g. carboxymethylcellulose or hydroxycarboxymethylcellulose, fatty alcohols, monoglycerides and fatty acids, polyvinyl alcohol and polyvinylpyrrolidone. In particular, non-ionic thickeners are used.

In addition to preservatives, other germ-inhibiting agents can also be used and incorporated into the compositions according to the invention. Advantageous substances are, for example, 2,4,4'-trichloro-2'-hydroxydiphenylether (irgasan), 1,6-di-(4-chlorophenylbiguanido)-hexane (chlorhexidine), 3,4,4'-trichlorocarbanilide, quaternary ammonium compounds, clove oil, mint oil, thyme oil, triethyl citrate, farnesol (3,7,11-trimethyl-2,6,10-dodecatrien-1-ol) as well as agents or agent combinations described in the patent publications DE 37 40 186, DE 39 38 140, DE 42 04 321, DE 42 29 707, DE 43 09 372, DE-44 11 664, DE 195 41 967, DE 195 43 695, DE 195 43 696, DE 195 47 160, DE 195 02 108, DE 196 02 110, DE 196 02 111, DE 196 31 003, DE 196 31 004 and D-196 34 019 and the patent specifications DE 42 29 737, DE 42 37 081, DE 43 24 219, DE 44 29 467, DE 44 23 410 and DE 195 16 705. Sodium hydrogen carbonate can be used advantageously. Antimicrobial polypeptides can also be used.

Light filtering agents may also be contained. These agents absorb UV rays in the UV-B and/or UV-A range. Suitable UV filters are, for example, 2,4,6-triaryl-1,3,5-triazines in which the aryl groups can carry at least one substituent, respectively, preferably selected from hydroxy, alkoxy, especially methoxy, alkoxycarbonyl, especially methoxycarbonyl and ethoxycarbonyl, and mixtures thereof. Also suitable are p-aminobenzoic acid esters, cinnamic acid esters, benzophenones, camphor derivatives as well as pigments that keep out UV rays, such as titanium dioxide, talcum and zinc oxide.

Any UV-A and UV-B filter substances can be considered as UV filter substances. Examples that are to be mentioned:

The cosmetic and dermatological preparations according to the invention may also advantageously contain inorganic pigments based on metal oxides and/or other metal compounds which are insoluble or sparingly soluble in water, that keep out UV rays, selected from the group of oxides of zinc (ZnO), titanium ($TiO_2$), iron (z. B. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and mixtures of such oxides.

Suitable hyperemising substances may also be contained in the cosmetic or pharmaceutical compositions. These stimulate the blood circulation of the skin. Examples are essential oils such as mountain pine extract, lavender extract, rosemary extract, juniper berry extract, horse chestnut extract, birch leaf extract, hayf lower extract, ethyl acetate, camphor, menthol, peppermint oil, rosemary extract, eucalyptus oil, etc.

Also keratolytic and keratoplastic substances can be contained. Examples of such substances comprise salicylic acid, calcium thioglycolate, thioglycolic acid and their salts, sulphur, etc. Suitable anti-dandruff agents are sulphur, sulphur polyethylene glycol sorbitan monooleate, sulphur ricinol polyethoxylate, zinc pyrithione, aluminium pyrithione, etc.

Suitable antiphlogistic agents that counteract skin irritations are e.g. allantoin, bisabolol, dragosantol, chamomile extract, panthenol, etc.

Cosmetically or pharmaceutically acceptable polymers, such as cationic, amphoteric and neutral polymers. Suitable polymers are e.g. cationic polymers with the designation polyquaternium according to INCI e.g. copolymers of vinylpyrrolidone/N-vinylimidazolium salts (Luviquat FC, Luviquat HM, Luviquat MS, Luviquat Care), copolymers of N-vinylpyrrolidone/dimethylaminoethyl methacrylate, quaternized with diethyl sulfate (Luviquat PQ 11), copolymers of N-vinylcaprolactam/N-vinylpyrrolidone/N-vinylimidazolium salts (Luviquat E Hold), cationic cellulose derivatives (Polyquaternium-4 and -10), acrylamidocopolymers (Polyquaternium-7) and chitosan.

Suitable cationic (quaternized) polymers are also merquat (polymer based on dimethyldiallyl ammonium chloride), gafquat (quaternary polymers formed by the reaction of polyvinylpyrrolidone with quaternary ammonium compounds), polymer JR (hydroxyethylcellulose with cationic groups) and cationic polymers on plant basis, e.g. guar polymers such as the Jaguar brands of the company Rhodia.

Other suitable polymers are also neutral polymers such as polyvinylpyrrolidones, copolymers of N-vinylpyrrolidone and vinyl acetate and/or vinyl propionate, polysiloxanes, polyvinylcaprolactam and other copolymers with N-vinylpyrrolidone, polyethyleneimines and their salts, polyvinylamines and their salts, cellulose derivatives, polyaspartic acid salts and their derivatives. These include, for example, Luviflex® Swing (partially saponified copolymer of polyvinyl acetate and polyethylene glycol, company BASF).

Suitable polymers are also non-ionic, water-soluble or water-dispersible polymers or oligomers, such as polyvinylcaprolactam, e.g. Luviskol® Plus (BASF), or polyvinylpyrrolidone and their copolymers, in particular with vinyl esters, such as vinyl acetate, e.g. B. Luviskol® VA 37 (BASF), polyamides, e.g. based on itaconic acid and aliphatic diamines, as described e.g. in DE-A-43 33 238.

Suitable polymers are also amphoteric or zwitterionic polymers, such as the octylacrylamide/methyl methacrylate/tert.-butylaminoethylmethacrylate-hydroxypropyl-methacrylate copolymers available under the names Amphomer (National Starch) as well as zwitterionic polymers, such as those disclosed for example in the German patent applications DE 39 29 973, DE 21 50 557, DE 28 17 369 and DE 3708 451. Acrylamidopropyltrimethylammonium chloride/acrylic acid or methacrylic acid copolymers and their alkali and ammonium salts are preferred zwitterionic polymers. Further suitable zwitterionic polymers are methacroylethylbetaine/methacrylate copolymers, which are commercially available under the name Amersette (AMERCHOL), and copolymers of hydroxyethylmethacrylate, methylmethacrylate, N,N-dimethylaminoethylmethacrylate and acrylic acid (Jordapon (D)). Suitable polymers are also non-ionic, siloxane-containing, water-soluble or dispersible polymers, e.g. polyethersiloxanes such as Tegopren® (company Goldschmidt) or Besi (company Wacker).

A further subject of the invention relates to foods or food supplements containing the concentrates according to the invention.

As far as the prepared products are foods to which the concentrates are added directly, they are comestibles of any kind. For example, bakery products, alcoholic or non-alcoholic beverages, fruit-based lemonades, (carbonised) isotonic beverages, (carbonised) soft drinks, nectars, spritzers, fruit and vegetable juices, fruit or vegetable juice preparations and dairy products are to be named. Preferably, these are comestibles which do not need to be heated during preparation.

If the products are food supplements, they are generally used without any other additives, with the exception of pure packaging materials. Macro or micro capsules are a preferred form of application. Macrocapsules preferably consist of gelatin or they are spray-dried products containing polysaccharides or dextrins as a base.

According to one embodiment, the cosmetic composition or the pharmaceutical composition further comprises 0.01-10 wt.-% of a skin soothing agent and/or an antioxidant.

Examples of skin soothing agents or emollientia suitable for a topical composition comprise bisabolol, allantoin, menthol, sucrose, centella extract, glycryrrhiza extract, farnesol, ruscus extract, mallow extract, jasmine extract, rosemary acid and plant extracts containing rosemary acid, oat extract, ginger extract, [6]-paradol, hamamelis extract, calendula extract, arnica extract, echinacea extract, hydrogenated polyisobutene, C-12-C15 alcohol benzoates, isopropyl myristate, mineral oils, lanolin and lanolin derivatives, triglycerides, such as for example coconut oil, cetostearyl alcohol, cetyl alcohol, isopropyl palmitate, capryl/caprin triglyceride, PPG-2 myristyl ether propionate, dimethicone, methicone, petrolatum and other skin soothing agents commonly known by the skilled person.

Antioxidants are preferably selected from amino acids (e.g. glycine, histidine, tyrosine, tryptophane) and derivatives thereof, imidazoles (e.g. urocanic acid) and derivatives thereof, peptides such as D,L-carnosine, D-carnosine, L-carnosine and derivatives thereof (e.g. B. Anserine), carotenoids, carotenes (e.g. β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thiorodoxine, glutathione, cysteine, cystine, cystamine and their glycosyl, N-acetyl, methyl, ethyl, propyl, amyl, butyl and lauryl, palmitoyl, oleyl, y-linoleyl, cholesteryl and glyceryl esters) and their salts, di laurylthiodipropionate, distearylthiodipropionate, thiodipropionic acid and derivatives thereof (esters, ethers, peptides, lipids, nucleotides, nucleosides and salts) and sulfoximine compounds (e.g. B. buthionine sulfoximines, homocysteine sulfoximines, buthionine sulfones, penta-, hexa-, heptathionine sulfoximine), especially in very low, compatible dosages (e.g. pmol to μmol/kg range), further (metal)-chelators (e.g. d-hydroxy fatty acids, palmitic acid, phytic acid, lactoferrin), o-hydroxy acids (e.g. citric acid, lactic acid, malic acid), humic acid, bile acid, bile extracts, biliverdin, EDTA and derivatives thereof, unsaturated fatty acids and derivatives thereof (e.g. v-linolenic acid, linoleic acid, oleic acid), folic acid and derivatives thereof, ubiquinone and ubiquinolv and derivatives thereof, vitamin C and derivatives thereof (e.g. sodium ascorbate, ascorbyl palmitate, Mg ascorbyl phosphate, ascorbyl acetate), tocopherol and derivatives thereof (e.g. vitamin E acetate, tocotrienol), vitamin A and derivatives (vitamin A palmitate) as well as coniferylbenzoate of benzoic resin, rutinic acid and derivatives thereof, o-glycosylrutin, ferulic acid, furfurylidene glucitol, carnosine, butylhydroxytoluene, butyl hydroxyanisole, nordihydroguaiac resin acid, nordihydroguaiaretic acid, trihydroxybutyrophenone, [6]-paradol, 4-hydroxyacetophenone, uric acid and derivatives thereof, mannose and derivatives thereof, zinc and derivatives thereof (for example ZnO, ZnSO4), selenium and derivatives thereof (e.g. selenomethionine), stilbenes and derivatives thereof (e.g. stilbene oxide, trans-stilbene oxide).

According to one embodiment, the use of yarrow is provided to stimulate the expression of heat shock proteins (HSP) and/or antimicrobial peptides (AMPs) in skin cells.

The human skin is a border organ and provides protection against, amongst others, environmental influences. The human skin is constantly exposed to a large number of potentially dangerous microorganisms. Despite this threat from microorganisms, the skin is extremely resistant to infections. Several studies carried out over the last decade show a chemical defense system present in the skin based on the production of antimicrobial peptides and proteins (AMPs). The AMPs represent a diverse group of small molecules (12-100 amino acid residues) that make up the main effector system of innate immunity. They provide the first line of defense against pathogens. AMPs produced in response to a hazard can quickly provide a broad spectrum of microbes, such as bacteria, fungi, viruses or protozoa, through their broad spectrum of effective antimicrobial activity. AMPs have been identified in a variety of exposed tissues or surfaces such as skin, eyes, ears, mouth, respiratory tract, lungs, intestines, and urinary tract. In human skin, they can be produced either constitutively by resident skin cells or by infiltrating immune cells or in response to a risk such as infection, trauma, wound healing or chronic inflammation. AMPs are produced in human skin mainly by keratinocytes, neutrophils, sebocytes or sweat glands. In several diseases of the human skin, there is a reciprocal correlation between the severity of the disease and the level of AMP production. Skin injuries in patients with atopic dermatitis show decreased expression of defensins and cathelicidine LL-37. Increased levels of AMPs are also associated with burns and chronic wounds. In contrast, overexpression of AMPs can lead to increased protection against skin infections, as observed in patients with psoriasis and rosacea and inflammatory skin infections, which rarely lead to a superinfection. The defensins comprising alpha and beta families represent one of the largest and most studied families of AMPs in mammals. They are produced by a variety of skin and bone marrow-derived cells, exhibit a broad spectrum of antimicrobial activity against gram-positive and gram-negative bacteria, viruses, fungi and some protozoa, and are important components of the innate immune system. Beta defensins are cationic peptides with antimicrobial activity that defend epithelial surfaces including the skin, gastrointestinal, urinary, and respiratory tract. Human β-defensin 1 peptide (hBD-1) is encoded by the DEFB1 locus and is active against gram-positive and negative bacteria. After the reduction of the disulfide bridges, hBD-1 becomes an effective AMP against the opportunistic pathogenic fungus *Candida albicans*. It shows a synergistic effect with LL-37 or lysozyme against *S. aureus* and *E. coli*.

S100 proteins are low molecular weight cationic proteins characterised by two calcium-binding EF hand motifs. They are involved in a multitude of cellular processes, such as for example calcium-dependent cell signaling, cell growth, and defense against microbes. S100 Calcium binding protein A8 (S100A8) is a protein encoded by the S100A8 gene in humans. S100A8 (calgranulin A) and S100A9 (calgranulin B) form an antimicrobial heterodimeric complex also known as calprotectin in epidermal keratinocytes. It has been shown that the S100A8/S100A9 complex also has antimicrobial activity against bacteria such as for example *Escherichia coli, Klebsiella* spp., *Staphylococcus aureus, S. epidermis, Capnocytophaga sputigena* and *Borrelia burgdorferi* as well as antifungal activity against the fungus *Candida albicans*.

Heat shock proteins (HSPs) are molecular chaperones that prevent cell death. Organisms and cells react to various stress conditions, such as environmental, metabolic and pathophysiological stress, by selectively upregulating HSPs. They are identified by their increased expression after a heat shock (usually one hour or more at temperatures of 3-5° C. above normal). The assumption that HSPs protect cells from heat damage is supported by the following facts: 1) HSP expression occurs exactly in parallel with the development and decline of thermal tolerance (resistance to killing by heat); 2) mutation or inactivation of HSPs impairs a cell's ability to survive at high temperatures; 3) overexpression of HSPs can often improve a cell's ability to withstand high temperatures. The induction of the heat shock protein HSP70 in human keratinocytes and NIH/3T3 fibroblasts by cinnamic acid derivatives, amongst others chlorogenic acid, is described for example in U.S. Pat. No. 9,265,743.

These proteins are classified into six major families based on their molecular weight, i.e. Hsp100, Hsp90, Hsp70, Hsp60, Hsp40 and small heat shock proteins (sHsps). sHsps have subunit molecular weights of 12-43 kDa. The ability to prevent aggregation of proteins and polypeptides, especially under stress conditions, that lead to an unfolding of cellular proteins, is the most important function of many sHSPs. Human sHSPs have very different characteristics with respect to their heat-induced expression, tissue and intracellular localization, structure, substrate preference and function. Because of this difference, human sHSPs have different capacities to protect against acute and different types of chronic (disease-related) stress.

HSP27 belongs to the small heat shock proteins (sHSPs). It is an ATP-independent molecular chaperone that protects against stress-induced protein aggregation. Hsp27 is found in intact skin mainly in the granular and prickle-cell layer of the epidermis.

According to one embodiment, the use of yarrow for increasing the thermal tolerance of the skin is provided.

The thermal tolerance of the skin concerns an inducible phenomenon in which cells become resistant to an otherwise damaging or lethal heat stress after a heat stress. It can be taken from Maytin E. et al. (J. Invest. Dermatol 1990; 95: 635-42; J. Biol Chem. 1992; 267: 231 89-96; J. Invest Dermatol 1995; 104 [4]: 448-55, Farage M A. Textbook of Aging Skin. Springer-Verlag Berlin Heidelberg 2010) that heat stress on human keratinocytes not only leads to thermal tolerance and to an increase in heat shock protein synthesis, but also to insensitivity to other stressing stimuli such as heavy metals, hypoxia and, surprisingly, also to a resistance to UVB-induced damages.

According to one embodiment, the yarrow is used as yarrow fresh plant press juice or as a cosmetic composition in the use according to the invention.

According to one embodiment, when used according to the invention, the dosage of yarrow fresh plant press juice concentrate in the cosmetic composition is 0.0001-10 wt.-% based on 100 wt.-% of the cosmetic composition.

Preferably, the dosage of yarrow fresh plant press juice concentrate in cosmetic compositions, in particular in cosmetic compositions for cleansing and caring for skin and hair, is 0.001-5 wt.-% and more preferably 0.005-3 wt.-%.

According to one embodiment, the pharmaceutical composition according to the invention is used as a medicament.

The pharmaceutical composition according to the invention can also be used in cancer prevention and in the treatment of skin diseases.

It is known that in diseases such as atopic dermatitis, actinic keratosis, a precursor of skin cancer, psoriasis, rosacea and other skin diseases characterised by barrier damage and chronic inflammation, heat shock protein synthesis in the corresponding skin regions is reduced and the repair mechanisms of the skin are disturbed. In the controlled apoptosis of keratinocytes, disturbances occur and the immune defense is weakened. Parallel to these processes, inflammatory enzymes such as matrix metalloproteinases are increasingly formed. Skin ageing and inflammation are characterised by the fact that the repair mechanisms of the skin are disturbed and weakened and inflammation mediators are increasingly released.

In particular, the pharmaceutical composition according to the invention can be used to avoid and/or alleviate skin damage within the framework of cancer therapy. This use of the pharmaceutical composition according to the invention is based on the discovered mode of action of yarrow, in particular of the ingredients of yarrow, which increase the thermal tolerance in the skin. It can be assumed that this effect is due to the expression of heat shock proteins in skin cells. This effect can be used to protect healthy skin cells from the effects of medication and/or radiation in the context of cancer therapy, in particular radiotherapy of skin cancer. The antimicrobial properties of yarrow also support this protective effect on human skin.

According to one embodiment, when yarrow is used according to the invention or the pharmaceutical composition is used according to the invention for use as a medicament, topical application to the skin and/or hair takes place.

In the context of the present invention, the term "have" or "having" refers to an open enumeration and does not exclude other components or steps in addition to the expressly mentioned components or steps. Where, in the context of the present invention, a composition is described using the expression "have" or "having", this expressly includes compositions consisting of the named components or essentially consisting of the named components.

In the context of the present invention, the term "consisting of" refers to an exhaustive enumeration and excludes any other components or steps apart from the components or steps expressly mentioned.

In the context of the present invention, the term "essentially consisting of" refers to a partially exhaustive enumeration and refers to compositions which, in addition to the named components, contain only such further components which do not materially alter the character of the composition or which are present in quantities which do not materially alter the character of the composition.

Further features and advantages of the invention result from the following description of preferred execution examples.

EXAMPLES

All specifications given in the examples in % refer to specifications in wt.-% unless explicitly stated otherwise.

Example 1: Manufacturing of a Yarrow Fresh Plant Press Juice Concentrate by Freeze Drying 100 ml yarrow (*Achillea millefolium*) fresh plant press juice (company Schoenenberger), produced from the flowering herb cultivated in Germany, is frozen and subsequently freeze-dried. 5.3 g dry juice 1a is obtained as a brown-green solid and the composition is analysed:

TABLE 1

| Substance class | Content [wt.-%] |
| --- | --- |
| Total polyphenols (photometric, Folin-Denis method as catechin equivalents) Containing | 16.4 |
| Sum of monocaffeoylquinic acids (chlorogenic acid, neo- and cryptochlorogenic acid, HPLC)* | 10.5 |
| Sum of dicaffeoylquinic acids (1,5-, 3,4-, 3,5- and 4,5- dicaffeoylquinic acid, HPLC)* | 5.3 |
| Rutin (HPLC) | 0.3 |
| Total proteins (Nitrogen analyser) | 3.3 |
| Sum of amino acids (HPLC) | 1.0 |
| Potassium $K^+$ (IC) | 10.2 |
| Calcium $Ca^{2+}$ (IC) | 0.7 |
| Magnesium $Mg^{2+}$ (IC) | 0.4 |
| Sodium $Na^+$ (IC) | 0.04 |
| Water (Karl Fischer) | 7.5 |

*Quantified as chlorogenic acid

Three further batches of yarrow (*Achillea millefolium*) fresh plant press juice (company Schoenenberger) of 100 ml each are frozen and subsequently freeze-dried. The obtained dry juices 1b-1d are weighed and analysed for the sum of mono- and dicaffeoylquinic acids and rutin:

TABLE 2

| Substance class | 1a | 1b | 1b | 1d | Average |
|---|---|---|---|---|---|
| Yield of freeze-dried yarrow fresh plant press juice Content [wt.-%] | 5.3 | 4.5 | 4.9 | 4.1 | 4.7 ± 0.4 |
| Sum of monocaffeoylquinic acids (chlorogenic acid, neo- and cryptochlorogenic acid, HPLC)* | 10.5 | 8.9 | 11.4 | 7.7 | 9.6 ± 1.3 |
| Sum of dicaffeoylquinic acids (1,5-, 3,4-, 3,5- and 4,5-dicaffeoylquinic acid, HPLC)* | 5.3 | 3.9 | 5.7 | 3.1 | 4.5 ± 1.0 |
| Rutin (HPLC) | 0.3 | 0.4 | 0.3 | 0.1 | 0.3 ± 0.1 |
| Water (Karl Fischer) | 7.5 | n.d. | n.d. | 5.6 | 6.6 ± 1.0 |

*Quantified as chlorogenic acid
n.d. = not determined

The results show that the 4 batches of yarrow (*Achillea millefolium*) fresh plant press juice (company Schoenenberger) contain on average 4.7±0.4 dry residue.

The freeze-dried yarrow fresh plant press juice concentrates contain on average only 6.6±1.0% water, 9.6±1.3% sum of monocaffeoylquinic acids, 4.5±1.0% sum of dicaffeoylquinic acids and 0.3±0.1% rutin.

Example 2: Manufacturing of a Yarrow Fresh Plant Press Juice Concentrate by Spray Drying 1 l yarrow fresh plant press juice (company Schoenenberger, dry matter content 5.3%) is mixed with 150 g maltodextrin DE 17-20 and spray dried. Obtained is a beige, free-flowing powder consisting of 75% maltodextrin and 25% yarrow dry fresh plant press juice. The spray-dried concentrate is analysed for the sum of mono- and dicaffeoylquinic acids and rutin:

TABLE 3

| Substance class | Content [wt.-%] |
|---|---|
| Sum of monocaffeoylquinic acids (chlorogenic acid, neo- and cryptochlorogenic acid, HPLC)* | 2.9 |
| Sum of dicaffeoylquinic acids (1,5-, 3,4-, 3,5- and 3,4-dicaffeoylquinic acid, HPLC)* | 1.4 |
| Rutin (HPLC) | 0.1 |
| Water (Karl Fischer) | 3.9 |

*Quantified as chlorogenic acid

The analytical results show that the ingredients remain unchanged during spray drying and no degradation takes place.

Example 3: Effect of Yarrow Fresh Plant Press Juice Concentrate on the Gene Expression of Heat Shock Proteins in Skin Cells Neonatal human epidermal keratinocytes (nHEKs) are seeded in microtiter plates with 6 wells in a density of $0.2 \times 10^6$ cells/cavity and cultured in EpiLife medium. After an incubation period of 24 hours, the yarrow fresh plant press juice concentrate from example 1 is applied in a concentration of 0.005 wt.-% in EpiLife and incubated for 24 hours.

The isolation and purification of the mRNA takes place with the aid of the RNeasy® Mini Kit from the company Qiagen. Elution of the mRNA from the column takes place with 50 µl RNase free water. The quantification and determination of the purity of the isolated RNA takes place spectrophotometrically. The purity is assessed by the ratios of the extinctions E260/E280 and E260/E230. The transcription of RNA into cDNA takes place according to the manufacturer's instructions (RNA-to-cDNA Kit, Applied Biosystems). The amount transcribed is 0.5-1 µg per 6-well. The transcribed samples are immediately processed in the PCR or stored at −20° C. until the experiment is continued.

TABLE 4

Transcription conditions for the reverse transcription

| Step | Duration [min] | Temp. [C. °] | Number of cycles |
|---|---|---|---|
| Reverse transcription | 60 | 37 | |
| Enzyme inactivation | 5 | 95 | |
| Holding a temperature | until the device is stopped | 4 | until the device is stopped |

The qRT-PCR takes place in the next step. For qRT-PCR, the cDNA is thawed and mixed with the TaqMan® Fast Universal PCR Master Mix (2×) (Life Technologies). The TaqMan® plate with 96 wells (Life Technologies, Darmstadt) can be individually equipped with the desired primers. Into each well of the 96 well array plate a volume of 10 µL of sample is pipetted and the wells are carefully airtightly sealed with an adhesive film (MicroAmp®) and centrifuged. Gene expression analysis takes place in the StepOne Plus Fast Real-Time PCR Instrument (Applied Biosystems). After the heating phase, the device automatically runs through the cycles shown in table 5 one after the other.

TABLE 5

The set PCR cycles

| Step | Duration [sec] | Temp. [C. °] | Number of cycles |
|---|---|---|---|
| Initial cDNA denaturation | 20 | 95 | 1 |
| cDNA denaturation | 3 | 95 | 40 |
| Annealing and elongation | 30 | 60 | 40 |

The measured values are exported and evaluated in MS Office Excel. The relative gene expression is calculated according to the ΔΔCT method. In the first step of the calculation, the ΔCT value is calculated for each sample by subtracting the CT value of the reference gene (gene HRPT) from the CT value of the gene to be examined.

$$\Delta CT\text{value}_{target\ gene} = CT\text{value}_{target\ gene} - CT\text{value}_{reference\ gene\ (HTRP\ gene)}$$

After standardisation, the ΔCT value of the control sample (untreated) is subtracted from the ΔCT value of the treated sample (PS applied).

$$\Delta\Delta CT\text{value}_{target\ gene} = \Delta CT\text{value}_{treated} - \Delta CT\text{value}_{control}$$

In the last step, the relative expression difference (relative quantification value (RQ value)) between the stimulated sample (PS applied) and control is calculated. Relative gene expression (RQ value) = $2^{-\Delta\Delta CT}$ An RQ value of >2.5 is considered a relevant induction of a gene.

TABLE 6

Results

| Cell type | NHEK |
|---|---|
| Test concentration | 0.005% |
| RQ values | |
| HPRT1 (housekeeping gene) | 1.0 |
| HSPB2 → HSP27 | 8.0 |
| ASPA1L → HSP70 | No relevant induction |

The results show that yarrow fresh plant press juice very effectively upregulates the gene expression of heat shock protein HSP27 at a very low test concentration, but has no effect on HSP70.

Example 4: Effect of Yarrow Fresh Plant Press Juice Concentrate on the Gene Expression of AMPs in Skin Cells HaCaT cells are seeded in microtiter plates with 6 wells in a density of $0.5 \times 10^6$ cells/well and cultured in EpiLife medium.

After an incubation period of 2 days, the yarrow fresh plant press juice concentrate from example 1 is applied in a concentration of 0.005 wt.-% in EpiLife and incubated for 24 hours.

The isolation and purification of the mRNA takes place with the aid of the RNeasy® Mini Kit from the company Qiagen. Elution of the mRNA from the column takes place with 50 µl RNase free water. The quantification and determination of the purity of the isolated RNA takes place spectrophotometrically. The purity is assessed by the ratios of the extinctions E260/E280 and E260/E230.

The transcription of the RNA into cDNA takes place according to the manufacturer's instructions (RNA-to-cDNA Kit, Applied Biosystems). The amount transcribed is 0.5-1 µg per 6-well. The transcribed samples are immediately processed in the PCR or stored at −20° C. until the experiment is continued.

TABLE 7

Transcription conditions for the reverse transcription

| Step | Duration [min] | Temp. [C. °] | Number of cycles |
|---|---|---|---|
| Reverse transcription | 60 | 37 | |
| Enzyme inactivation | 5 | 95 | |
| Holding a temperature | until the device is stopped | 4 | until the device is stopped |

The qRT-PCR takes place in the next step. For the qRT-PCR, the cDNA is thawed and mixed with the TaqMan® Fast Universal PCR Master Mix (2×) (Life Technologies). The TaqMan® plate with 96 wells (Life Technologies, Darmstadt) can be individually equipped with the desired primers. Into each well of the 96 well array plate a volume of 10 µL of sample is pipetted and the wells are carefully airtightly sealed with an adhesive film (MicroAmp®) and centrifuged again for one minute. Gene expression analysis takes place in the StepOne Plus Fast Real-Time PCR Instrument (Applied Biosystems). After the heating phase, the device automatically runs through the cycles shown in Table 8 one after the other.

TABLE 8

The set PCR cycles

| Step | Duration [sec] | Temp. [C. °] | Number of cycles |
|---|---|---|---|
| Initial cDNA denaturation | 20 | 95 | 1 |
| cDNA denaturation | 3 | 95 | 40 |
| Annealing and elongation | 30 | 60 | 40 |

The measured values are exported and evaluated using MS Office Excel. The relative gene expression is calculated according to the ΔΔCT method. In the first step of the calculation, the ΔCT value is calculated for each sample by subtracting the CT value of the reference gene (gene HRPT) from the CT value of the gene to be examined.

$$\Delta CT\text{value}_{target\ gene} = CT\text{value}_{target\ gene} - CT\text{value}_{reference\ gene\ (HTRP\ gene)}$$

After standardization, the ΔCT value of the control sample (untreated) is subtracted from the ΔCT value of the treated sample (PS applied).

$$\Delta\Delta CT\text{value}_{target\ gene} = \Delta CT\text{value}_{treated} - \Delta CT\text{value}_{control}$$

In the last step, the relative expression difference (relative quantification value (RQ value)) between stimulated sample (PS applied) and control is calculated.

Relative gene expression (RQ value) = $2^{-\Delta\Delta CT}$

An RQ value of >2.5 is considered a relevant induction of a gene.

TABLE 9

Results

| Cell type | HaCaT |
|---|---|
| Test concentration | 0.005% |
| RQ values | |
| HPRT1 (housekeeping gene) | 1.0 |
| DEFB1 → beta-defensin 1 | 9.1 |
| S100A8 → calgranulin A | 2.7 |

The results show that yarrow fresh plant press juice very effectively upregulates the gene expression of the antimicrobial peptides beta-defensin 1 and S100 calcium binding protein A8 at very low test concentrations.

Example 5: Formulation examples

1=Soothing balm for the skin
2=Tinted anti-aging balm, SPF 15
3=After-sun moisturizing spray O/W
4=Night cream W/O
5=Facial cleansing gel
6=After-shave hydrogel
7=Anti-dandruff hair shampoo
8=Antiperspirant pump spray
9=Day care fluid for skin lightening O/W
10=Cream to restore the barrier function O/W
11=Sun protection lotion SPF 24 (UVA/UVB balance)

In the formulation examples 1-11, the two perfume oils PFO1 and PFO2 described below are used as fragrances, respectively (DPG=dipropylene glycol).

TABLE 10

Perfume oil PFO1 with rose scent

| Component | Amount (in wt.-%) |
|---|---|
| Acetophenone, 10% in DPG | 10 |
| n-Undecanal | 5 |
| Aldehyde C14 (so-called peach aldehyde) | 15 |
| Allylamylglycolate, 10% in DPG | 20 |
| Amylsalicylate | 25 |
| Benzyl acetate | 60 |
| Citronellol | 80 |
| d-Limonene | 50 |
| trans-9 Decenol | 15 |
| Dihydromyrcenol | 50 |
| Dimethylbenzylcarbinyl acetate | 30 |
| Diphenyl oxide | 5 |
| Eucalyptol | 10 |
| Geraniol | 40 |
| Nerol | 20 |
| Geranium oil | 15 |
| cis-3 Hexenol, 10% in DPG | 5 |
| cis-3 Hexenyl salicylate | 20 |
| Indol, 10% in DPG | 10 |
| Alpha ionone | 15 |
| Beta ionone | 5 |
| Lilial ® (2-Methyl-3-(4-tert-butyl-phenyl)propanal) | 60 |
| Linalool | 40 |
| Methylphenyl acetate | 10 |
| Phenylethyl alcohol | 275 |
| Styrolyl acetate | 20 |
| Terpineol | 30 |
| Tetrahydrolinalool | 50 |
| Cinnamyl alcohol | 10 |
| Total | 1000 |

TABLE 11

Perfume oil PFO2 with white flowers and musk scent

| Component | Amount (in wt.-%) |
|---|---|
| Benzyl acetate | 60 |
| Citronellyl acetate | 60 |
| Cyclamen aldehyde (2-methyl-3-(4-isopropylphenyl)propanal | 20 |
| Dipropylene glycol (DPG) | 60 |
| Ethyllinalool | 40 |
| Florol (2-isobutyl-4-methyltetrahydro-2H-pyran-4-ol) | 30 |
| Globanone ® [(E/Z)-8-cyclohexadecen-1-one] | 180 |
| Hedione ® (Methyldihydrojasmonate) | 140 |
| Hexenylsalicylate, cis-3 | 10 |
| Vertocitral (2,4-dimethyl-3-cyclohexenecarboxaldehyde) | 5 |
| Hydratropa aldehyde, 10% in DPG | 5 |
| Isodamascone (1-(2,4,4-trimethyl-2-cyclohexen-1-yl)-2-buten-1-one), 10% in DPG | 5 |
| Isomuscone (cyclohexadecanone) | 40 |
| Jacinthaflor (2-methyl-4-phenyl-1,3-dioxolane) | 10 |
| Cis-jasmone, 10% in DPG | 20 |
| Linalool | 50 |
| Linalyl acetate | 30 |
| Methyl benzoate, 10% in DPG | 25 |
| para-Methylcresol, 10% in DPG | 10 |
| Nerol | 20 |
| Phenylpropyl aldehyde | 5 |
| 2-Phenylethyl alcohol | 82 |
| Tetrahydrogeraniol | 13 |
| 2,2-Dimethyl-3-cyclohexyl-1-propanol | 80 |
| Total: | 1000 |

TABLE 12

Cosmetic formulations (quantities in wt.-%)

| Components | 1 | 2 | 3 | 4 | 5 | 6 | 7 | 8 | 9 | 10 | 11 |
|---|---|---|---|---|---|---|---|---|---|---|---|
| Spray-dried yarrow fresh plant press juice concentrate containing 75% maltodextrin Maltodextrin, *Achillea millefolium* extract | | 1.2 | | | 0.5 | 0.1 | | | 0.3 | | 0.02 |
| Yarrow fresh plant press juice concentrate, 10% dry residue *Achillea millefolium* extract, Glycerin | | 2.5 | | | | 1 | 0.02 | | | | |
| Freeze-dried yarrow fresh plant press juice concentrate *Achillea millefolium* extract | 0.01 | | | 0.002 | | | | | | 0.05 | |
| Actipone © Laminaria Saccharina Glycerin, Water (Aqua), *Laminaria saccharina* extract | | | | | | 0.3 | | | | | |
| Allantoin Allantoin | 0.1 | | | | | 0.1 | | | | | |
| *Aloe Vera* Gel Conc. 10:1 *Aloe barbadensis* (Aloe) leaf juice | | | | | | 1 | | | | | |
| Aluminium Stearate Aluminium stearate | | | | | 1.2 | | | | | | |
| Beta arbutin Arbutin | | | | | | | | | 1 | | |
| Arlypon ® F Laureth-2 | | | | | | | 2 | | | | |
| Avocado Oil *Persea gratissima* (avocado) oil | | | 3 | | | | | | | | |
| Betulin 90% Betulin | | | | | | | | | | 0.1 | |
| Biotive L-Arginine Arginine | | 0.6 | | | | | | | | | 0.5 |
| Biotive Troxerutin Troxerutin | | 0.5 | | | | | | | | | 0.5 |
| (−)-alpha-Bisabolol Bisabolol | | | | | | | | | | | 0.1 |

TABLE 12-continued

Cosmetic formulations (quantities in wt.-%)

| Components | 1 | 2 | 3 | 4 | 5 | 6 | 7 | 8 | 9 | 10 | 11 |
|---|---|---|---|---|---|---|---|---|---|---|---|
| Carbopol Aqua SF-1 Polymer Acrylates copolymer | | | | | 5 | | | | | | |
| Carbopol ® Ultrez-10 Carbomer | | 0.2 | | | | 0.4 | | | 0.2 | | |
| CeramideBIO ® Cetylhydroxyproline palmitamide | | | | | | | | | | 0.5 | |
| Citric acid 10% in water | | | | | 0.2 | | 0.5 | | | | |
| Covi-Ox ® T-70 Tocopherol | | | 0.1 | | | | | | | | |
| Crinipan ® AD Climbazole | | | | | | | 0.3 | | | | |
| Cutina ® PES Pentaerythrityl distearate | | 2 | | | | | | | | | |
| D-Panthenol Panthenol | 1 | | 1 | | | 0.5 | 0.5 | | | | |
| Dehyton K Cocamidopropyl betaine | | | | | | 8 | | 8 | | | |
| Dermacryl ® AQF Acrylates Copolymer | | | | | | | | | | | 2 |
| Dow Corning 200(100 cs) Silicone fluid dimethicone | 2 | 2 | | | | | | | 0.5 | 0.5 | |
| Dow Corning 246 Fluid Cyclohexasiloxane, Cyclopentasiloxane | | | 2 | | | | | | | | 3 |
| Dracorin ® CE Glyceryl stearate citrate | | | | | | | | | | 1.5 | |
| Dracorin ® GMS Glyceryl stearate | | | | | | | | | | 2 | |
| Dracorin ® GOC Glyceryl oleate citrate, Caprylic/Capric triglyceride | | | 2 | | | | | | | | |
| Dragocalm ® Water (aqua), Glycerin, *Avena sativa* (oat) kernel extract | 1 | | | | | | | | | | |
| Dragocid ® Liquid Phenoxyethanol, Methyl paraben, Ethyl paraben, Butyl paraben, Propyl paraben, Isobutyl paraben | | | | | | | | | 0.8 | | |
| Dragoderm ® Glycerin, *Triticum vulgare* (wheat) gluten, Water (aqua) | | | | | | | | 0.5 | | | |
| Dragosan ® W/O P Sorbitan isostearate, Hydrogenated castor oil, Ceresin, Beeswax (Cera Alba) | | | | 8 | | | | | | | |
| Dragosantol ® 100 Bisabolol | | | | | 0.2 | | | | | | |
| Dragosine ® Carnosine | | | 0.2 | | | | | | | | |
| Dragoxat ® 89 Ethylhexyl Isononanoate | | 5 | | 7 | | | | | | 2 | 2 |
| Disodium EDTA | 0.1 | 0.1 | | | | | | | 0.1 | | 0.1 |
| Emulsiphos ® Potassium cetyl phosphates, Hydrogenated palm glycerides | | 2 | | | | | | | 1.5 | 2 | 2 |
| Ethanol | | | | | 5 | | 8 | | | | |
| Extrapone ® Aloe vera Water (aqua), *Aloe barbadensis*, Propylene glycol, Alcohol | | | | | | 2 | | | | | |
| Extrapone ® Witch Hazel Propylene glycol, *Hamamelis virginiana* (Witch Hazel) Water, Water (Aqua), *Hamamelis virginiana* (Witch Hazel) extract | 1 | | | | | | | | | | |
| Extrapone ® Rosemary Glycerin, Water (aqua), *Rosmarinus officinalis* (rosemary) leaf extract | | | | | | | 0.3 | | | | |
| Extrapone ® Seaweed Water (Aqua), Butylene glycol, *Fucus vesiculosus* extract | | | | | | 0.5 | | | | | |
| Farnesol DT Phenoxyethanol, Farnesol, Bisabolol | | | | | | | | | 0.2 | | |
| Food coloring brown E172 + E171 Powder | | | 2 | | | | | | | | |
| Frescolat ® MGA Menthone glycerin acetal | | | | 0.1 | | | | | | | |

TABLE 12-continued

Cosmetic formulations (quantities in wt.-%)

| Components | 1 | 2 | 3 | 4 | 5 | 6 | 7 | 8 | 9 | 10 | 11 |
|---|---|---|---|---|---|---|---|---|---|---|---|
| Frescolat ® ML<br>Menthyl lactate | | | 0.5 | | | 0.3 | 0.2 | | | | |
| Frescolat ® X-Cool<br>Menthyl ethylamido oxalate | | | | | | | | | | 0.2 | |
| Genapol ® LRO Liquid<br>Sodium laureth sulphate | | | | | | | 37 | | | | |
| Givobio ® GZN<br>Zinc gluconate | | | | | | | | | | 0.5 | |
| Glycerin | 1.5 | | 4 | 3 | | | | | 3.5 | 3 | 3 |
| Hydrolite ® 5<br>Pentylene glycol | 3 | | 5 | | 2 | 5 | | 5 | | | 2 |
| Hydroviton-24 ®<br>Water (aqua), Pentylene glycol, Glycerin, Lactic acid, Sodium lactate, Serine, Urea, Sorbitol, Sodium chloride, Allantoin | | | | 1 | | | | | | | |
| Hydroviton ® Plus 2290<br>Water (aqua), Pentylene glycol, Glycerin, Fructose, Urea, Citric acid, Sodium hydroxide, Maltose, Sodium PCA, Sodium chloride, Sodium lactate, Trehalose, Allantoin, Sodium hyaluronate, Glucose | | | | | | | | 1 | | 2 | |
| Isoadipate<br>Diisopropyl adipate | | | | | | | | | 2 | | |
| Isodragol ®<br>Triisononanoin | 1 | | | | | | | | | 3 | 2 |
| Jojoba Oil<br>Simmondsia Chinensis (Jojoba) Seed Oil | | | | 2 | | | | | | | |
| Potassium sorbate | | | 0.1 | | | | | | | | |
| Keltrol ® CG-RD<br>Xanthan gum | | 0.2 | | | | | | | 0.2 | | 0.4 |
| Kojic acid | | | | | | | | | 0.5 | | |
| Kojic acid | | | | | | | | | | | |
| Lanette ® 16<br>Cetyl alcohol | | | | | | | | | 1.5 | | 1 |
| Lanette ® O<br>Cetearyl alcohol | | | | | | | | | | 2 | 0.5 |
| Lara Care ® A-200<br>Galactoarabinan | | | | | | | | | | | 0.3 |
| Locron ® L<br>Aluminium chlorohydrate | | | | | | | | 16 | | | |
| Magnesium sulphate | | | | 0.7 | | | | | | | |
| Mineral oil | | | | 8 | | | | | | | |
| Sodium ascorbyl phosphate | | | | | | | | | 1 | | |
| Sodium chloride | | | | | | | 0.1 | | | | |
| Sodium hydroxide 10% in water | 1 | | | | 2 | 0.7 | | | 0.2 | 0.3 | |
| Neo Heliopan ® 303<br>Octocrylene | | 4 | | | | | | | | | 10 |
| Neo Heliopan ® 357<br>Butylmethoxydibenzoyl methane | | 2 | | | | | | | 2 | | 3 |
| Neo Heliopan ® AP,<br>15% solution, neutralized with L-Arginine Aqua, Disodium phenyl dibenzimidazole tetrasulfonate, Arginine | | 6.7 | | | | | | | | | 6.7 |
| Neo Heliopan ® AV<br>Ethylhexyl methoxycinnamate | | | | | | | | | 7.5 | | |
| Neo Heliopan ® BB<br>Benzophenone-3 | | | | | | | | | 3 | | |
| Neo Heliopan ® E 1000<br>Isoamyl p. methoxycinnamate | | | | | | | | | | | 1 |
| Neo Heliopan ® HMS<br>Homosalate | | | | | | | | | 10 | | 5 |
| Neo Heliopan ® OS<br>Ethylhexyl salicylate | | 3 | | | | | | | 5 | | |
| Neo Heliopan ® Hydro,<br>20% solution, neutralized with biotive arginine Aqua, Phenylbenzimidazole, Sulphonic acid, Arginine | | 10 | | | | | | | | | 10 |
| Neo-PCL Water Soluble N<br>Trideceth-9, PEG-5 Ethylhexanoate, Water (aqua) | | | | | | 1 | 1.5 | 2 | | | |

TABLE 12-continued

Cosmetic formulations (quantities in wt.-%)

| Components | 1 | 2 | 3 | 4 | 5 | 6 | 7 | 8 | 9 | 10 | 11 |
|---|---|---|---|---|---|---|---|---|---|---|---|
| Neutral Oil<br>Caprylic/Capric Triglyceride | | | 5 | | | | | | | 10 | |
| Niacinamide | | | | | 1 | | | | | | |
| Ozokerite Wax 2389<br>Ozokerite | | | | 2 | | | | | | | |
| Perfume oil PFO1 or PFO2<br>Perfume | 0.05 | 0.3 | 0.25 | 0.3 | | 0.1 | 0.5 | 0.7 | 0.3 | 0.1 | 0.2 |
| PCL-Liquid 100<br>Cetearyl ethylhexanoate | 3 | 2 | 4 | 5 | | | | | | | |
| PCL-Solid<br>Stearyl heptanoate, Stearyl caprylate | 1 | | 0.5 | | | | | | | | |
| Pemulen ® TR-2<br>Acrylates/C10-30 Alkyl acrylate crosspolymer | 0.6 | | 0.25 | | | | | | | | |
| Phenethyl alcohol | | | | | 0.2 | | | | | | |
| Phenoxyethanol | | | | | | | | | | | 0.2 |
| Phytoconcentrole ®<br>Shea butter<br>Glycine soy (soybean) oil,<br>*Butyrospermum parkii* (shea butter) | | 1 | | | | | | | | | |
| Polymer JR 400<br>Polyquaternium-10 | | | | | | | | 0.4 | | | |
| Propylene glycol-1,2<br>Propylene glycol | | | | | | 5 | | 3 | | | |
| Silcare Silicone 41M65 Stearyl dimethicone | | | | | | | | | | | 1 |
| Solubilizer<br>PEG-40 Hydrogenated castor oil,<br>Trideceth-9, Propylene glycol,<br>Water (Aqua) | | | | | | | | 3 | | | |
| Suletal LA<br>Ammonium lauryl sulphate | | | | | 12 | | | | | | |
| SymCalmin ®<br>Butylene glycol, Pentylene glycol,<br>Hydroxyphenyl propamidobenzoic acid | 1 | | | | | | | 0.1 | | 0.1 | |
| SymClariol ®<br>Decylene glycol | | | 0.5 | | 1 | | | | | 0.3 | |
| SymDecanox HA<br>Caprylic/Capric Triglyceride,<br>Hydroxymethoxyphenyl decanone | | | 2 | | | | | | | | |
| SymDeo ® B125<br>2-Methyl 5-cyclohexylpentanol | | | | | | | | 0.2 | | | |
| SymDeo ® MPP<br>Dimethyl phenyl 2-butanol | | | | | | | | 0.5 | | | |
| Symdiol ® 68<br>1.2-Hexanediol, Caprylyl glycol | 1 | 0.5 | | | | | | | | | 0.3 |
| SymFinity ® 1298<br>*Echinacea purpurea* extract | | | | 0.05 | | | | | | | |
| SymGlucan ®<br>Water (Aqua), Glycerin, Beta-glucan | 1 | | 5 | | | | | | | | 2 |
| SymHair ® Force 1631<br>Pentylene glycol,<br>*Isochrysis galbana* extract | | | | | | | | 2 | | | |
| SymHelios ® 1031<br>Benzylidene dimethoxydimethylindanone | | 0.5 | | | | | | | | | |
| SymLift<br>Water, Trehalose, Glycerin,<br>Pentylene glycol, Beta-glucan,<br>*Hordeum vulgare* seed extract,<br>Sodium hyaluronate, 1,2-Hexanediol,<br>Caprylyl glycol, Sodium benzoate,<br>Maltodextrin | | 2 | | | | | | | | | |
| SymMatrix<br>Maltodextrin, *Rubus fruticosus*<br>(Blackberry) leaf extract | | | 0.1 | 0.3 | | | | | | | |
| SymMollient ® W/S<br>Trideceth-9, PEG-5<br>Isononanoate, Water (Aqua) | | | | | | 2 | 2 | | | | |
| SymOcide ® C<br>o-Cymen-5-ol | | | | | | 0.1 | | | | | |
| SymOcide ® PH<br>Phenoxyethanol,<br>Hydroxyacetophenone,<br>Caprylyl glycol, Water (Aqua) | | | | | | | | 1.0 | | | |

TABLE 12-continued

Cosmetic formulations (quantities in wt.-%)

| Components | 1 | 2 | 3 | 4 | 5 | 6 | 7 | 8 | 9 | 10 | 11 |
|---|---|---|---|---|---|---|---|---|---|---|---|
| SymOcide ® PS Phenoxyethanol, Decylene Glycol, 1,2-Hexanediol | | | | | | | | | | 0.8 | |
| SymOcide ® PT Phenoxyethanol, Tropolone | | | | 0.8 | | | | | | | |
| SymPeptide ® 225 Glycerin, Water (aqua), Myristoyl pentapeptide-11 | | | | 1 | | | | | | | |
| SymRelief ® 100 Bisabolol, Zingiber officinale (Ginger) root extract | | | | | | 0.2 | | | | | |
| SymRelief S Bisabolol, Hydroxymethoxyphenyl Decanone | | | | | | | | | | 0.1 | |
| SymRepair ® 100 Hexyldecanol, Bisabolol, Cetylydroxyproline Palmitamide, Stearic acid, Brassica campestris (rapeseed) sterols | | 1 | | 3 | | | | | | | |
| SymSave ® H Hydoxyacetophenone | | 0.5 | | | 0.8 | 0.5 | | | | 0.5 | |
| SymSol ® PF-3 Water (Aqua), Pentylene glycol, Sodium lauryl sulfoacetate, Sodium oleoyl sarcosinate, Sodium chloride, Disodium sulfoacetate, Sodium oleate, Sodium sulfate | | | | | | 1.3 | | | | | |
| SymSitive ® 1609 Pentylene glycol, 4-t-Butylcyclohexanol | | | 0.5 | | | | | | 0.5 | | |
| SymVital ® AgeRepair 3040 Zingiber officinale (ginger) root extract | | | 0.1 | | | | | | | | |
| SymWhite ® 377 Phenylethyl resorcinol | | | | | | | | | 0.5 | | |
| Tamasterol ® Phytosterols | | | | | | | | | | 0.3 | |
| Tapioca Pure Tapioca starch | | | | | | | | | | | 5 |
| Tegosoft ® PC 31 Polyglyceryl-3 caprate | | | | | | | | | | 0.3 | |
| Triethanolamin | | | 0.3 | | | | | | | | |
| Vitamin A Palmitate Retinyl Palmitate | | | | 0.1 | | | | | | | |
| Vitamin E Acetate Tocopheryl Acetate | | 0.5 | | 0.2 | | | | | | 0.3 | 0.5 |
| Zetesol LA-2 Ammonium laureth sulfate | | | | | 26 | | | | | | |
| Water | | | | | | Ad 100 | | | | | |

TABLE 13

Gel toothpaste

| Component | I (%) | II (%) | III (%) |
|---|---|---|---|
| Sodium carboxymethylcellulose | 0.40 | 0.40 | 0.40 |
| Sorbitol 70%, in water | 72.00 | 72.00 | 72.00 |
| Polyethylene glycol (PEG) 1500 | 3.00 | 3.00 | 3.00 |
| Sodium saccharinate | 0.07 | 0.07 | 0.07 |
| Sodium fluoride | 0.24 | 0.24 | 0.24 |
| p-Hydroxybenzoic acid (PHB) ethyl ester | 0.15 | 0.15 | |
| SymDiol 68 | | | 0.5 |
| SymSave H | | | 0.25 |
| Peppermint aroma | 1.00 | 1.00 | 1.00 |
| Spray-dried yarrow fresh plant press juice concentrate containing 75% maltodextrin | 0.5 | | 0.1 |
| Yarrow fresh plant press juice concentrate, 10% dry residue in glycerin/water | | 1 | |
| Abrasive silica | 11.00 | 11.00 | 11.00 |
| Thickening silica | 6.00 | 6.00 | 6.00 |
| Sodium dodecyl sulphate (SDS) | 1.40 | 1.40 | 1.40 |
| Dist. water | ad 100.00 | ad 100.00 | ad 100.00 |

TABLE 14

Ready-to-use mouthwash with fluoride

| Component | I (%) | II (%) | III (%) |
|---|---|---|---|
| Ethanol | 7.00 | 7.00 | |
| Glycerin | 12.00 | 12.00 | |
| Sodium fluoride | 0.05 | 0.05 | 0.18 |
| Pluronic F-127 ® (BASF, surface active substance) | 1.40 | 1.40 | |
| Sodium phosphate buffer pH 7.0 | 1.10 | 1.10 | |
| Sorbic acid | 0.20 | 0.20 | |

TABLE 14-continued

Ready-to-use mouthwash with fluoride

| Component | I (%) | II (%) | III (%) |
|---|---|---|---|
| Sodium saccharinate | 0.10 | 0.10 | 0.10 |
| Cinnamon/menthol aroma | 0.15 | 0.15 | 0.15 |
| Spray-dried yarrow fresh plant press juice concentrate containing 75% maltodextrin | 0.05 | | 0.8 |
| Yarrow fresh plant press juice concentrate, 10% dry residue in glycerin/water | | 0.5 | |
| Dye | 0.01 | 0.01 | 0.01 |
| Sorbitol 70% | | | 10 |
| Cremophor RH455 | | | 1.8 |
| SymDiol 68 | | | 0.5 |
| SymSave H | | | 0.2 |
| Dist. water | ad 100.00 | ad 100.00 | ad 100.00 |

The invention claimed is:

1. A spray dried yarrow fresh plant press juice concentrate comprising:
 10 to 50 wt. % of yarrow fresh plant press juice dry residue,
 0 to 10 wt. % of water,
 50 to 90 wt. % of carrier(s) chosen from maltodextrin, dextrin, cyclodextrin, and mixtures thereof, and
 one or more dicaffeoylquinic acid(s);
 wherein the percent by weight is based on the total weight of the spray dried yarrow fresh plant press juice concentrate.

2. The spray dried yarrow fresh plant press juice concentrate according to claim 1, wherein the yarrow fresh plant press juice concentrate further comprises preservatives and/or stabilizers.

3. A method for manufacturing the spray dried yarrow fresh plant press juice concentrate of claim 1 comprising:
 mixing yarrow fresh plant press juice with carrier(s) chosen from maltodextrin, dextrin, cyclodextrin, and mixtures thereof, and
 spray drying the mixture of yarrow fresh plant press juice and carrier(s).

4. The method according to claim 3, wherein the spray drying is performed at a temperature of 200 to 400° C.

5. A cosmetic composition comprising the spray dried yarrow fresh plant press juice concentrate according to claim 1.

6. A pharmaceutical composition, food composition, or food supplement comprising the spray dried yarrow fresh plant press juice concentrate according to claim 1.

7. A cosmetic composition according to claim 5, further comprising: 0.01 to 10 wt. % of a skin soothing agent and/or an antioxidant.

8. A pharmaceutical composition according to claim 6, further comprising:
 0.01 to 10 wt. % of a skin soothing agent and/or an antioxidant.

9. A method for treating skin and/or hair comprising topically applying to the skin and/or hair the spray dried yarrow fresh plant press juice concentrate according to claim 1.

10. The method according to claim 9, wherein the method comprises stimulating the expression of heat shock proteins (HSP) in skin cells of the skin.

11. The method according to claim 9, wherein the method increases the thermal tolerance of the skin.

12. A method for treating skin and/or hair comprising topically applying to the skin and/or hair the cosmetic composition according to claim 5.

13. The method of claim 12, wherein the cosmetic composition comprises 0.0001 to 10 wt. % of the spray dried yarrow fresh plant press juice concentrate, based on the total weight of the cosmetic composition.

14. The spray dried yarrow fresh plant press juice concentrate according to claim 1, wherein the one or more dicaffeoylquinic acid(s) is/are chosen from 1,5-dicaffeoylquinic acid, 3,4-dicaffeoylquinic acid, 3,5-dicaffeoylquinic acid, and 4,5-dicaffeoylquinic acid.

* * * * *